(12) United States Patent
Coomber et al.

(10) Patent No.: US 8,557,744 B2
(45) Date of Patent: Oct. 15, 2013

(54) MEMBRANE-TRANSLOCATING PEPTIDES

(75) Inventors: David Coomber, Orange (AU); Kevin Fitzgerald, Essex (GB); Duncan McGregor, Suffolk (GB); Chris Ullman, Cambridge (GB); Tomas Leanderson, Malmö (SE)

(73) Assignee: Isogenica Ltd., Cambridgeshire (GB)

( * ) Notice: Subject to any disclaimer, the term of this patent is extended or adjusted under 35 U.S.C. 154(b) by 498 days.

(21) Appl. No.: 11/996,496

(22) PCT Filed: Jul. 24, 2006

(86) PCT No.: PCT/GB2006/002766
§ 371 (c)(1), (2), (4) Date: May 30, 2008

(87) PCT Pub. No.: WO2007/010293
PCT Pub. Date: Jan. 25, 2007

(65) Prior Publication Data
US 2008/0287311 A1 Nov. 20, 2008

(30) Foreign Application Priority Data

Jul. 22, 2005 (GB) .................................. 0515115.4

(51) Int. Cl.
*C40B 30/04* (2006.01)
*C12Q 1/70* (2006.01)

(52) U.S. Cl.
USPC ........ 506/9; 506/7; 435/375; 536/22; 530/350

(58) Field of Classification Search
USPC .............. 506/9, 7; 435/375; 536/22; 530/350
See application file for complete search history.

(56) References Cited

U.S. PATENT DOCUMENTS

| | | | |
|---|---|---|---|
| 7,348,420 B2 * | 3/2008 | Klaenhammer et al. ..... | 536/23.1 |
| 2003/0082615 A1 | 5/2003 | Reed et al. | |
| 2004/0197867 A1 | 10/2004 | Titus et al. | |

FOREIGN PATENT DOCUMENTS

| | | |
|---|---|---|
| WO | WO 99/49879 A | 10/1999 |
| WO | WO 00/58488 A2 | 10/2000 |
| WO | WO 01/27154 A2 | 4/2001 |
| WO | WO 02/088318 A2 | 11/2002 |
| WO | WO 2004/022746 A | 3/2004 |
| WO | WO 2004/050871 A | 6/2004 |
| WO | WO 2004/081188 A | 9/2004 |
| WO | WO 2005/017188 A1 | 2/2005 |

OTHER PUBLICATIONS

Yonezawa et al (Nucleic Acids Research, 2003, vol. 31, No. 19 e118.*
Tawfik et al ,Nature Biotechnology vol. 16, Jul. 1998, 652-656.*
Ivanenkov et al,Biochimica et Biophysica Acta, 1999, 1448, 450-462.*
Search Report, United Kingdom Patent Application No. GB0515115.4, Dec. 20, 2005, 3 Pages.
European Patent Office Communication, European Patent Application No. 06765092.9, Sep. 4, 2008, 10 pages.
European Patent Office Communication, European Patent Application No. 06765092.9, May 15, 2009, 4 pages.
European Patent Office Communication, European Patent Application No. 06765092.9, Jan. 11, 2010, 3 pages.
Gao C., et al., "A cell-penetrating peptide from a novel pVII-pIX phase-displayed random peptide library," Biorganic & Medicinal Chemistry, Dec. 2002, pp. 4057-4065, Vo. 10, No. 12.
Persson, D., et al., "Application of a novel analysis to measure the binding of the membrane-translocating peptide penetratin to negatively charged liposomes," Biochemistry, Jan. 21, 2003, pp. 421-429, vol. 42, No. 2.
Tseng, Y.L., et al., "Translocation of liposomes into cancer cells by cell-penetrating peptides penetratin and tat: a kinetic and efficacy study," Molecular Pharmacology, Oct. 2002, pp. 864-872, vol. 62, No. 4.
Torchilin, V.P., et al., "TAT peptide on the surface of liposomes affords their efficient intracellular delivery even at low temperature and in the presence of metabolic inhibitors," Proceedings of the National Academy of Sciences of USA, National Academy of Science, Washington, DC, Jul. 17, 2001, pp. 8786-8791, vol. 98, No. 15.
Odegrip, R., et al., "CIS display in vitro selection of peptides from libraries of protein—DNA complexes" PNAS 101 (9) 2004, pp. 2806-2810.
PCT International Search Report and Written Opinion, PCT/GB2006/002766, Nov. 14, 2006, 16 Pages.

* cited by examiner

*Primary Examiner* — Teresa D. Wessendorf
(74) *Attorney, Agent, or Firm* — Fenwick & West LLP

(57) ABSTRACT

A method is selects membrane-translocating peptides (MTPs) from a peptide display library that are capable of crossing or penetrating a lipid membrane. A plurality of nucleic acid constructs that encode displayed peptides are expressed, resulting in the formation of a plurality of nucleic acid-peptide complexes, each complex comprising at least one displayed peptide associated with the corresponding nucleic acid construct encoding the displayed peptide; the complexes are exposed to a population of membrane-encapsulated compartments, allowing a translocating reaction to occur; complexes that remain unassociated with the membrane are removed; optionally complexes that are associated with the membrane are removed; and internalized nucleic acid-peptide complexes are recovered. The membrane-encapsulated compartments may be artificial vesicles such as liposomes, or populations of one or more cell types.

12 Claims, 2 Drawing Sheets

Figure 1:
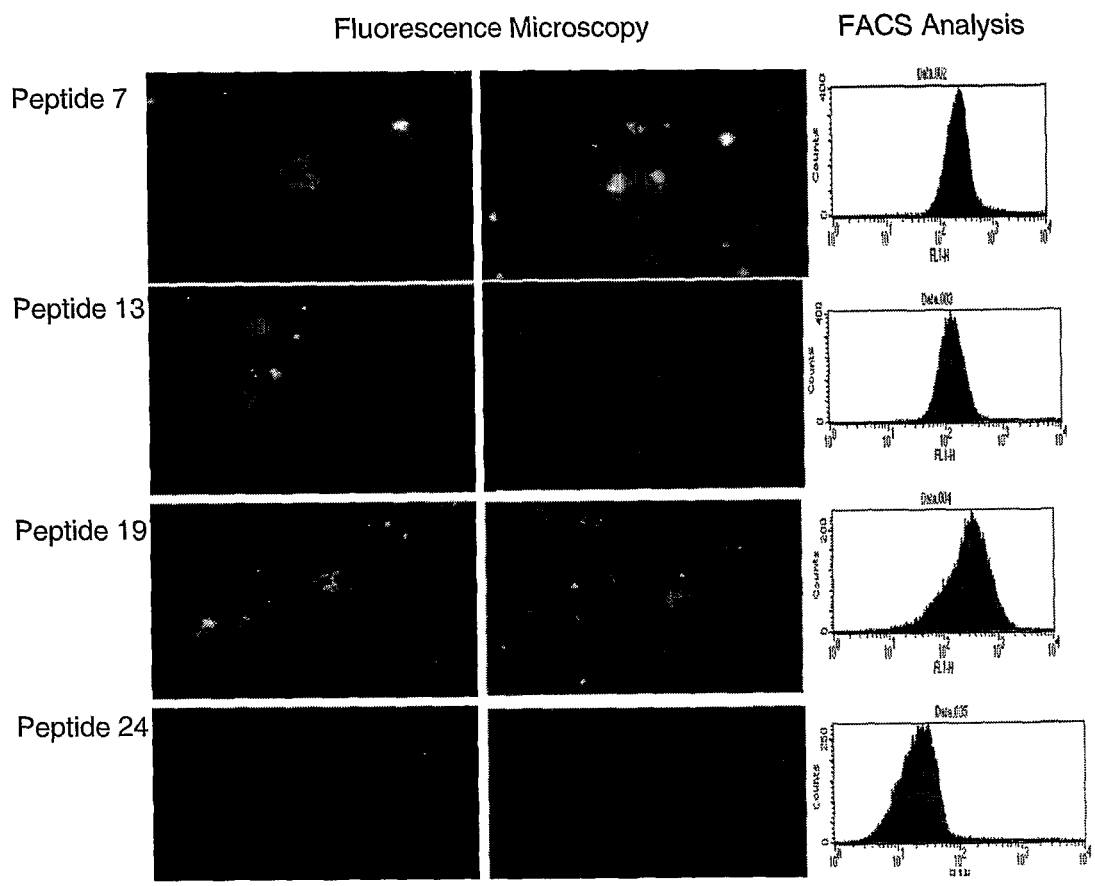

```
D4        :     IKSSHGR-----RW----SNKDRKYSHS
                   SHGR    R     SNKD+
HIV-TAT   : 46  LGISHGRKKRKHRRGTPQSNKDHQNPV
```

Figure 2

SEQUENCE LISTING

<160> NUMBER OF SEQ ID NOS: 1

<210> SEQ ID NO 1
<211> LENGTH: 19
<212> TYPE: PRT
<213> ORGANISM: Artificial
<220> FEATURE:
<223> OTHER INFORMATION: Selected MTP - D4

<400> SEQUENCE: 1

Ile Lys Ser Ser His Gly Arg Arg Trp Ser Asn Lys Asp Arg Lys Tyr
1               5                   10                  15

Ser His Ser

MEMBRANE-TRANSLOCATING PEPTIDES

This application is the National Stage of International Application No. PCT/GB2006/002766, filed Jul. 24, 2006, which claims priority to GB Patent application No. 0515115.4, filed on Jul. 22, 2005 which is incorporated by reference in its entirety.

FIELD OF THE INVENTION

This invention relates to methods for the isolation of novel compounds termed membrane-translocating peptides (MTPs). Such MTPs are characterised by the ability to transport themselves and non-translocating moieties associated with the MTP across membranes.

BACKGROUND OF THE INVENTION

The ability to deliver nucleic acids, proteins, peptides, amino acids, small molecules, viruses, etc. (hereafter referred to collectively as "non-translocating moieties") into cells or into specific cell types is useful for various applications in oncology, developmental biology, gene therapy and in the general understanding of the mode of operation of particular proteins, nucleic acids and small molecules in a model system. Most therapeutically important proteins and peptides do not readily translocate across biological membranes. However, some transactivating factors and homeoproteins have been shown to be capable of facilitating membrane translocation, including Tat derived peptides (Fawell et al., 1994 *Proc. Natl. Acad. Sci. USA* 91:664-668), the third helix of the antennapedia homeodomain protein (Derossi et al., 1994, *J. Biol. Chem.* 269:10444-10450; U.S. Pat. Nos. 5,888,762 and 6,015,787), and VP22 (Schwarze et al., 2000, *Trends Pharmacol. Sci.* 21:45-48). Such naturally derived peptides are often isolated in membrane vesicles within the cytoplasm of the cell, which often prevents the associated non-translocating moiety from accessing its desired target (Potocky et al. 2003, *J Biol. Chem.* 278: 50188-94).

To date, novel peptides have been engineered through the use of two different approaches. The first approach produces candidate peptides by chemically synthesizing a randomized library of 6-10 amino acid peptides (J. Eichler et al., 1995, *Med. Res. Rev.* 15:481-496; K. Lam, 1996, *Anticancer Drug Des.* 12:145-167; M. Lebl et al., 1997, *Methods Enzymol.* 289:336-392). In the second approach, candidate peptides are synthesized by cloning a randomized oligonucleotide library into an Ff filamentous phage gene, which allows peptides that are much larger in size to be expressed on the surface of the bacteriophage (H. Lowman, 1997, *Ann. Rev. Biophys. Biomol. Struct.* 26:401-424; G. Smith et al., 1993, *Meth. Enz.* 217:228-257). Randomized peptide libraries up to 38 amino acids in length have also been made, and longer peptides are likely achievable using this system. The peptide libraries that are produced using either of these strategies are then typically mixed with a pre-selected matrix-bound protein target. Peptides that bind are eluted, and their sequences are determined. From this information new peptides are synthesized and their biological properties are determined. Phage display has previously been used to identify translocating peptides, but relatively few peptides have been isolated by this method, and those that have are generally cell type specific and require endocytosis for entry into a cell (Gao et al. 2002, *Bioorg Med. Chem.*, 10: 4057-65). One disadvantage associated with prior art peptides that rely on endocytosis to cross the cellular membrane is that typically such a mechanism results in the delivery of the translocating peptide, and any associated non-translocating moiety, to endosomes where they are both destroyed without causing the desired cellular effect.

A further disadvantage of the prior art is that the size of the libraries that can be generated with both phage display and chemical synthesis is limited to within the $10^6$-$10^9$ range. This limitation has resulted in the isolation of peptides of relatively low affinity, unless a time-consuming maturation process is subsequently used. This library-size limitation has led to the development of techniques for the in vitro generation of peptide libraries including mRNA display (Roberts, & Szostak, 1997, *Proc. Natl. Acad. Sci. USA*, 94, 12297-12302), ribosome display (Mattheakis et al., 1994, *Proc. Natl. Acad. Sci. USA*, 91, 9022-9026) and CIS display (Odegrip et al., 2004, *Proc. Natl. Acad. Sci. USA*, 101 2806-2810) amongst others. These libraries are superior to phage display libraries in that the size of libraries generated by such methods is 2-3 orders of magnitudes larger than is possible with phage display. This is because unlike techniques such as phage display, there are no intermediate in vivo steps.

However, at present no methods have been described using known in vitro display systems that allow for the specific and selective identification of membrane-translocating peptides (MTPs). Moreover, such methods could allow for the identification of MTPs that are capable of crossing layers of cells, such as endothelium.

Hence, there remains a need for methods that could provide a much needed advance in the field of MTP discovery and peptide drug development.

SUMMARY OF THE INVENTION

The present invention provides a method for the selection of novel compounds, referred to as membrane-translocating peptides or MTPs, that are capable of translocating themselves and a non-translocating moiety across lipid membranes such as cell membranes. The MTPs of the present invention are selected for their ability to efficiently internalize associated moieties into membrane-encapsulated compartments, including a wide variety of cell types both in vivo and in vitro. The identified MTP of the invention can also comprise a molecule useful for diagnostic or therapeutic purposes.

Accordingly, in a first aspect of the invention there is provided a method for isolating a compound that exhibits membrane-translocation activity from a peptide display library, said library comprising a plurality of nucleic acid sequences that encode displayed peptides, comprising the steps of:
 a) expressing a plurality of nucleic acid constructs,
  wherein each nucleic acid construct comprises a promoter sequence operably linked to the nucleic acid sequence, such that expression of the plurality of nucleic acid constructs results in formation of a plurality of nucleic acid-peptide complexes, each complex comprising at least one displayed peptide associated with the corresponding nucleic acid construct encoding the displayed peptide;
 b) exposing the plurality of nucleic acid-peptide complexes to a population of membrane-encapsulated compartments, and allowing a translocating reaction to occur;
 c) removing any nucleic acid-peptide complexes that remain unassociated with the membrane-encapsulated compartments; and
 d) recovering any internalised nucleic acid-peptide complexes from within the membrane-encapsulated compartments, and characterising the peptide encoded by the nucleic acid sequence as comprising a membrane-translocating peptide (MTP).

In a preferred embodiment of the invention, the membrane-encapsulated compartment is a cell. Thus, the invention provides a method for isolating a compound that exhibits cell membrane-translocation activity from a peptide display library, said library comprising a plurality of nucleic acid sequences that encode displayed peptides, comprising the steps of:

a) expressing the plurality of nucleic acid constructs,
   wherein each nucleic acid construct comprises a promoter sequence operably linked to the nucleic acid sequence, such that expression of the plurality of nucleic acid constructs results in formation of a plurality of nucleic acid-peptide complexes, each complex comprising at least one peptide associated with the corresponding nucleic acid construct encoding the displayed peptide;
b) exposing the nucleic acid-peptide complexes to a population of one or more cell types and allowing a translocating reaction to occur;
c) removing any nucleic acid-peptide complexes that remain unassociated with the one or more cell types; and
d) recovering any internalised nucleic acid-peptide complexes from within the cells and characterising the peptide encoded by the nucleic acid sequence as comprising a membrane-translocating peptide (MTP).

In an alternative embodiment, the membrane-encapsulated compartment is preferably a lipid vesicle. For example, an artificially constituted lipid-encapsulated compartment, such as a micelle or liposome. Preferably, the lipid vesicle is a liposome. Preferably, the membrane comprises a lipid bilayer.

In further specific embodiments of the above inventions, the method further comprises a step after part (c) of removing nucleic acid-peptide complexes that are bound to the surface of the membrane-encapsulated compartment (e.g. a liposome or one or more cell types), but which have not been internalised. Hence, the methods of the invention preferably further comprise the step of: (c') removing cell surface associated nucleic acid-peptide complexes. This embodiment represents a further significant improvement in the art over phage display as it allows differentiation between surface-bound and internalized MTPs. Surprisingly, this significantly increases the number of MTPs that can be identified after one, two or more rounds of selection. Indeed after five rounds of selection with a CIS display library, 9/23 peptides were identified as MTPs (Example 1). In contrast, typically, in phage display selections to identify MTPs very low numbers of MTPs are found (Gao et al., 2002, *Bioorg. Med. Chem.* 10:4057-4065).

In another embodiment the membrane-translocating activity of the selected MTP does not involve or require endocytosis. Preferably, the MTP is capable of crossing the target membrane or membranes in the absence of an endocytotic mechanism. Thus in a preferred method, the one or more cell types are endocytosis incompetent, such as a red blood cell.

In another aspect of the invention, there is provided an MTP identified by the methods of the invention. Preferably, the MTP is an isolated peptide. The invention further encompasses derivatives of the MTPs of the invention. In another preferred embodiment, the MTP or derivative of the invention is linked to, associated with or attached/conjugated to a non-translocating moiety. The non-translocating moiety can be a peptide, a nucleic acid or another compound, as detailed hereinbelow. Advantageously, the means of linkage, association, attachment or conjugation is readily cleavable by means of an enzymatic reaction or other chemical process/degradation.

It is preferable if the membrane translocation event is uni-directional at least with respect to a portion of the compound that translocates across the membrane. This is advantageous because it is possible that the MTP may be capable of translocating both into and out of a membrane-encapsulated compartment. Thus, once the MTP has translocated into the membrane-encapsulated compartment, at least a portion of the peptide remains within the compartment. The portion of the peptide that remains within the compartment can be the MTP moiety itself, the associated non-translocating moiety, or both the MTP and the non-translocating moiety. Preferably, at least the non-translocating moiety remains within the membrane-encapsulated compartment, such as a target cell. Therefore, more preferably, the MTP is linked to, associated with, attached or conjugated to (e.g. by way of a cleavable bond) a non-translocating moiety, and after translocating into the membrane-encapsulated compartment, the non-translocating peptide is released from the MTP into the compartment or cell. Conveniently, the release of the non-translocating moiety is by way of an enzymatic cleavage or a chemical process e.g. chemical degradation, as further discussed below.

The invention further provides therapeutic molecules comprising an MTP conjugated to or functionally linked to a therapeutic molecule, such as a therapeutic peptide or nucleic acid. Conveniently, the therapeutic molecule is a non-translocating moiety as discussed above, including any compound useful as a therapeutic or diagnostic agent.

Non-limiting examples of non-translocating moieties and potential therapeutic molecules include nucleic acids (e.g. siRNA molecules), enzymes, hormones, cytokines, antibodies or antibody fragments, peptide fragments (e.g. peptides recognised by antibodies), analgesics, antipyretics, anti-inflammatory agents, antibiotics, antiviral agents, anti-fungal drugs, cardiovascular drugs, drugs that affect renal function and electrolyte metabolism, drugs that act on the central nervous system and chemotherapeutic drugs, to name but a few.

In a further aspect of the invention there is provided a nucleic acid molecule comprising a nucleic acid sequence encoding an MTP of the invention, optionally further encoding a non-translocating peptide or moiety and optionally further comprising regulatory nucleic acid sequences. An expression vector comprising a nucleic acid molecule of the invention is also provided.

In another aspect of the invention there is provided a composition (e.g. a therapeutic composition), comprising a membrane-encapsulated compartment, such as a liposome, and an MTP according to the invention. Preferably, the composition further comprises a non-translocating moiety conjugated to the MTP. Most preferably, the non-translocating moiety is a therapeutic molecule. Still more preferably, the therapeutic composition is prepared by adding one or more therapeutic molecules or MTPs according to the invention, or both, to a preparation of one or more liposome, and allowing a translocating event to take place.

The MTP libraries of the present invention are composed of, for example, peptides or peptide derivatives such as peptide mimetics and peptide analogues composed of naturally occurring or non-natural amino acids. According to the invention, the membrane-translocating peptides (MTPs) isolated by the invention are preferably non-naturally occurring amino acid sequences that are capable of crossing or spanning a lipid membrane, and preferably a lipid bilayer.

Typically, the MTPs of the invention are capable of crossing the target membrane, such that the peptide is released into the intra-membrane volume, i.e. the cytosol of a cell or the inner volume of a liposome. However, in some cases the MTP may merely insert into the target membrane, such that it spans the membrane. In this case, at least a portion of the MTP is within the membrane and preferably, at least either a portion of the MTP and/or an associated non-translocating moiety is within the intra-membrane volume. Preferably, the MTP of the invention is capable of crossing the target membrane and entering the cytoplasm of a cell, e.g. a red blood cell. Preferably the MTP is a non-naturally occurring amino acid sequence of between about 2 to 25 amino acids or about 8 and 20 amino acid residues.

Such compounds preferably are selected by the methods of the invention to enter the membrane-encapsulated compartment, e.g. a cell of interest, while remaining linked to the encoding nucleic acid, so that the nucleic acid to also transferred into the cell.

Specific examples of such compounds include linear or cyclic peptides, preferably between 2 and 25 amino acids or between about 8 and 20 amino acid residues in length, and combinations thereof, optionally modified at the N-terminus or C-terminus or both, as well as their salts and derivatives, functional analogues thereof, and extended peptide chains carrying amino acids or polypeptides at the termini of the sequences.

According to the invention, in vitro peptide display libraries are generated by a suitable means known to the person of skill in the art. For example, libraries of in vitro generated nucleic acid-peptide complexes may be suitably generated by an appropriate method such as described by Roberts, & Szostak, (1997, *Proc. Natl. Acad. Sci. USA*, 94, 12297-12302), Mattheakis et al., (1994, *Proc. Natl. Acad. Sci. USA*, 91, 9022-9026), Odegrip et al., (2004, *Proc. Natl. Acad. Sci. USA*, 101 2806-2810) and by WO2004/022746. In certain cases, such as where the maximum library size is within the limits of phage display technology or chemical synthesis, these methods may alternatively be used. The libraries of in vitro generated nucleic acid-peptide complexes are then selected according to their ability to translocate across (or at least span) a target membrane, e.g. a membrane of a cell type of interest.

In another step of the method of the invention, library members encoding MTPs are further selected by removing nucleic acid-peptide complexes encoding non-membrane-translocating peptides from the surface of the target membrane or cell with a suitable nuclease or protease or a combination of both. MTPs capable of crossing a membrane and thereby entering a cell or vesicle (e.g. a liposome) and transferring the associated nucleic acid moiety into the cell may then be recovered and characterised.

The invention also provides for the selection of a nucleic acid-peptide complex encoding an MTP linked to two or more MTPs or any other combinations that can be envisaged by one skilled in the art. For example, one or more (preferably each) of the members of the library of nucleic acid sequences may encode 2, 3, 4 or more MTP or potential MTP sequences. The invention further provides for the selection of a nucleic acid-peptide complex encoding an MTP linked to two or more non-translocating moieties.

All references cited herein are incorporated by reference in their entirety. Unless otherwise defined, all technical and scientific terms used herein have the same meaning as commonly understood by one of ordinary skill in the art to which this invention belongs.

The invention is further illustrated by the accompanying drawings in which

FIG. 1 shows a FACS analysis and fluorescent microscopy of non-fixed Jurkat cells. Peptides 7, 13, and 19 are examples of membrane-translocating peptides isolated by the method. Peptide 24 is a negative control FLAG epitope peptide.

FIG. 2 shows a peptide sequence comparison between a membrane-translocating peptide selected according to the method of the invention (identified as D4 (SEQ ID NO:1)) and the known membrane-translocating moiety of HIV-TAT.

DETAILED DESCRIPTION

In order to assist with the understanding of the invention several terms are defined herein.

The terms "peptide", "membrane-translocating peptide" or "MTP" as used herein refer to a plurality of amino acids joined together in a linear chain, including a dipeptide, tripeptide, oligopeptide and polypeptide. A dipeptide contains two amino acids; a tripeptide contains three amino acids; and the term oligopeptide is typically used to describe peptides having between 2 and about 50 or more amino acids. Peptides larger than about 50 are often referred to as polypeptides or proteins. For purposes of the present invention, the terms "peptide", and "membrane-translocating peptide" or "MTP" are not limited to any particular number of amino acids. Preferably, however, they contain about 2 to about 50 amino acids, or about 2 to about 40 amino acids, more preferably about 2 to about 30 amino acids or about 2 to about 25 amino acids. Most preferably the peptide or MTP contains from about 2 to about 20 amino acids or from 8 to about 20 amino acids. For example, an MTP identified according to the methods of the invention may be 18, 19. 20, 21, 22, 23, 24 or 25 amino acids in length. Typically, a membrane spanning domain of a protein is 22 to 25 amino acids in length, and therefore, particularly where the MTP spans rather than crosses a target membrane, the MTP may be 22, 23, 24 or 25 amino acids in length.

"Membrane-translocating peptides" (MTPs) as used herein are amino acid sequences (as described above), which may contain naturally as well as non-naturally occurring amino acid residues. Therefore, so-called "peptide mimetics" and "peptide analogues", which may include non-amino acid chemical structures that mimic the structure of a particular amino acid or peptide, may also be "membrane-translocating peptides" within the context of the invention. Such mimetics or analogues are characterized generally as exhibiting similar physical characteristics such as size, charge or hydrophobicity, and the appropriate spatial orientation that is found in their natural peptide counterparts. A specific example of a peptide mimetic compound is a compound in which the amide bond between one or more of the amino acids is replaced by, for example, a carbon-carbon bond or other non-amide bond, as is well known in the art (see, for example Sawyer, in *Peptide Based Drug Design*, pp. 378-422, ACS, Washington D.C. 1995).

The present invention is directed towards the identification and characterisation of MTPs from amongst a population (or library) of peptides—i.e. potential or putative MTPs that may be expressed from a library of nucleic acid sequences. Although the term 'peptide' is used herein, it will be understood that the present invention does not preclude identification of MTPs or larger peptide domains and motifs that would perhaps under conventional nomenclature be appropriately referred to as polypeptides or proteins.

Furthermore, the term "membrane-translocating peptide" (MTP) may include peptides that cross a membrane so that the MTP and any associated non-translocating moieties pass from one side of the membrane to the other, and peptides that merely "span" the target membrane. By "span" it is meant that an MTP may insert into (or penetrate) the target membrane so that at least a portion of the MTP remains within the membrane. Thus, for example, an MTP selected by the methods of the invention may span the target membrane causing a portion of the MTP to remain within the membrane (or lipid bilayer) and a portion of the MTP or an associated non-translocating moiety to be internalised (i.e. found on the inside of the respective vesicle or cell. Preferably, however, an MTP according to the invention crosses a target membrane, passing from one side of the membrane to the other side of the membrane. In one form, an MTP according to the invention is able to cross a plurality of membranes, such as a plurality of layers of Caco-2 cells or epithelium, such that the MTP is able to move from one side of a tissue to another side of the tissue, or to within the tissue layer.

By the term "derivative" of an MTP it is meant a peptide sequence that is capable of translocating itself and optionally also an associated/conjugated non-translocating moiety across a target membrane, but that comprises one or more mutations or modifications to the primary peptide sequence of an MTP identified by the methods of the invention. Thus, a derivative of an MTP may have one or more, e.g. 1, 2, 3, 4, 5 or more chemically modified amino acid side chains, which have been introduced into an MTP of the invention. In addition or in the alternative, a derivative of an MTP may contain one or more, e.g. 1, 2, 3, 4, 5 or more amino acid mutations, substitutions or deletions to the primary sequence of an MTP of the invention. Thus, the invention encompasses the results of maturation experiments conducted on an MTP to improve one or more characteristics of the MTP. For example, 1, 2, 3, 4, 5 or more amino acid residues of an MTP sequence may be randomly or specifically mutated using procedures known in the art (e.g. by modifying the encoding DNA or RNA sequence), and the resultant library/population of derivatised peptides may be selected according to pre-determined requirements (such as improved translocation into a particular cell-type, or improved selectivity of a particular cell-type), by any method known in the art. Selected peptides that display membrane-translocation capability are derivatives of MTPs and fall within the scope of the invention.

The term "membrane" in the context of the phrase "membrane-translocating", includes the membranes of any artificial or naturally occurring membrane that comprises a monolayer or bilayer of aliphatic molecules, such as fatty acid or lipid molecules. Thus, the term includes the membranes of micelles, liposomes, or other vesicles known to the person of skill in the art, and any type of naturally occurring cell, including bacterial, fungus, plant, animal or human, for example blood cells (e.g. red blood cells), or epithelial cells, including skin cells and gut wall cells. Preferably, the membrane is a lipid bilayer and it encapsulates an artificial liposome or an endocytotic-incompetent cell.

A "non-translocating moiety" as used herein, refers to an entity that cannot by itself cross a membrane, such as a lipid monolayer, bilayer or cell membrane; or to a moiety that cannot by itself cross such a membrane effectively enough to cause the desired intracellular effect. Such a non-translocating moiety includes nucleic acids and other polymers, peptides, proteins, peptide nucleic acids (PNAs), antibodies, antibody fragments, and membrane-impermeable small molecules amongst others. Preferably, a non-translocating moiety is a therapeutic molecule, which is further described elsewhere herein.

The term "amino acid" within the scope of the present invention is used in its broadest sense and is meant to include naturally occurring L α-amino acids or residues. The commonly used one and three letter abbreviations for naturally occurring amino acids are used herein (Lehninger, A. L., (1975) *Biochemistry*, 2d ed., pp. 71-92, Worth Publishers, New York). The correspondence between the standard single letter codes and the standard three letter codes is well known to one skilled in the art, and is reproduced here: A=Ala; C=Cys; D=Asp; E=Glu; F Phe; G=Gly; H His; I=Ile; K=Lys; L=Leu; M=Met; N=Asn; P=Pro; Q=Gln; R=Arg; S=Ser; T=Thr, V=Val; W=Trp; Y=Tyr. The general term "amino acid" further includes D-amino acids as well as chemically modified amino acids such as amino acid analogues, naturally occurring amino acids that are not usually incorporated into proteins such as norleucine, and chemically synthesized compounds having properties known in the art to be characteristic of an amino acid. For example, analogues or mimetics of phenylalanine or proline, which allow the same conformational restriction of the peptide compounds as do natural Phe or Pro, are included within the definition of amino acid. Such analogues and mimetics are referred to herein as "functional equivalents" of the respective amino acid. Other examples of amino acids are listed by Roberts and Vellaccio, *The Peptides: Analysis, Synthesis, Biology*, Gross and Meiehofer, eds., Vol. 5 p. 341, Academic Press, Inc., N.Y. 1983, which is incorporated herein by reference.

The present invention is directed towards the identification and characterisation of MTPs from amongst a population (or library) of peptides—i.e. potential or putative MTPs. In particular, the MTPs of the invention are selected using in vitro display of in vitro generated libraries of peptides.

The terms "in vitro display", "in vitro peptide display" and "in vitro generated libraries" as used herein refer to systems in which peptide libraries are expressed in such a way that the expressed peptides associate with the nucleic acids that encoded them, and in which such association does not follow the transformation of cells or bacteria with the said nucleic acids. Such systems contrast with phage display and other "in vivo display" systems in which the association of peptides with their encoded nucleic acids follows the transformation of cells or bacteria with the nucleic acids.

Membrane-translocating peptides, when used within the context of the present invention, may be "conjugated" to a non-translocating moiety. The term "conjugated" is used in its broadest sense to encompass all methods of attachment or joining that are known in the art. For example, the non-translocating moiety can be an amino acid extension of the C- or N-terminus of the MTP. In addition, a short amino acid linker sequence may lie between the MTP and the non-translocating moiety. The invention further provides for molecules where the MTP will be linked, e.g. by chemical conjugation to the non-translocating moiety optionally via a linker sequence. Typically, the MTP will be linked to the non-translocating moiety via a site in the non-translocating moiety that does not interfere with the activity of the non-translocating moiety. Here again, the MTP is considered to be "conjugated" to the non-translocating moiety. Optionally this linkage may be broken under reducing conditions found in the cytoplasm of cells after internalization.

As used herein, the term "conjugated" is used interchangeably with the terms "linked", "associated" or "attached". A wide range of covalent and non-covalent forms of conjugation are known to the person of skill in the art, and fall within the scope of the invention. For example, disulphide bonds, chemical linkages and peptide chains are all forms of covalent linkages. Where a non-covalent means of conjugation is preferred, the means of attachment may be, for example, a biotin-(strept)avidin link or the like. Antibody (or antibody fragment)-antigen interactions may also be suitably employed to conjugate an MTP of the invention to a non-translocating moiety. One suitable antibody-antigen pairing is the fluorescein-antifluorescein interaction.

In this manner a unidirectional and targeted delivery system can be made, whereby the means of conjugation between an MTP and a non-translocating moiety is preferably broken/cleaved once the MTP and its associated non-translocating moiety (or at least the non-translocating moiety itself) has crossed the target membrane. Any suitable combination of conjugation means and cleavage system can be used, such as enzymatic cleavage, ligand competition, radiation and the like. Preferably, when the target membrane is a cell membrane (such that the non-translocating moiety is delivered into a cell), the conjugation means is a peptide linkage that can be cleaved by an enzyme, preferably an endogenous enzyme, within the cell (e.g. in the cytoplasm). Alternatively, the conjugation is preferably a disulphide bridge that can be readily cleaved by the reducing intracellular environment of the cell. Where the membrane-encapsulated compartment is not a cell, e.g. it is a lipid vesicle, liposome, or the like, it may be preferable to use an alternative combination of conjugation means and cleavage means. Again, any suitable means can be used, provided (if desired) that the non-translocating moiety can be delivered unidirectionally to the interior of the compartment.

The non-translocating moiety may or may not be active in the conjugated form but in any case, is preferably active after it has been disassociated from the MTP (i.e. once the conjugation has been broken).

The present invention represents a significant advance in the art of peptide drug development by allowing screening of in vitro generated libraries for membrane-translocating properties. In vitro generated nucleic acid libraries encoding a plurality of peptides are synthesised and initially selected for binding to, penetration of (e.g. membrane spanning) or internalization into a target cell or liposome population. Library members incapable of associating with a target cell or liposome in one or more of the above ways are removed by washing or other appropriate methods known to those skilled in the art. By way of example, cells, liposomes (or other target membrane-encapsulated compartment) that are sufficiently dense may be spun through a non-aqueous layer of oil to separate the membrane-associated library members from the non-associated library members. Preferably, the oil is mineral oil. Other oils that may be suitable include oils with a specific gravity of less than water. In this regard, mineral oil has a specific density of 0.84 g/ml at 25° C. Preferably, cells such as red blood cells are separated from non-associated library members by centrifugation through mineral oil. As already noted above, an MTP may penetrate or cross the target membrane. Library members encoding an MTP or surface-binding peptide will remain bound to the target or internalized within the cell during this step.

Surface-bound library members are then removed from the cell surface by a non-specific protease such as trypsin, or a nuclease such as DNaseI, or a combination of both, or by any other method known to one skilled in the art. Only library members encoding an MTP remain within the cell population.

The internalized MTPs are then recovered and individually characterised by sequencing the associated nucleic acid, and for example, expressing or synthesising the encoded MTP to confirm the desired membrane-translocating properties. The eventual sub-cellular localization of the MTP may also be determined. As mentioned previously, such a step (i.e. the removal of membrane-bound library members from MTPs) is not possible with phage display libraries as these are naturally resistant to proteases such as trypsin (see e.g. WO-A-99058655), and a nuclease cannot be used as the phage nucleic acid is protected by the viral coat. A further limitation of phage display libraries is the inherent non-specific binding by phage particles to cell membranes, such non-specific binding being well known to those skilled in the art.

Advantageously, the MTPs of the invention are isolated and individually characterised. However, a mixed population of MTPs may be obtained by the methods of the invention, e.g. where more than one nucleic acid-peptide complex crosses a membrane and is internalised into, for example, a liposome or cell during the methods of the invention. In this event, the invention also encompasses said mixed population of MTPs.

Preferably, the invention provides MTPs that surprisingly can cross the cell membranes without endocytosis. Such MTPs can be further selected for by using cells in a selection with no known endocytotic transfer mechanism, such as red blood cells, or by using membrane-encapsulated compartments such as liposomes.

Optionally, the invention can be applied to the isolation of cell-type specific MTPs. In vitro generated nucleic acid libraries encoding a plurality of peptides are synthesised and selected for binding or internalization to a target cell population of interest, such as a population of cancer cells for example, after an earlier incubation with a different non-target cell population, in order to remove cross-reactive MTPs (i.e. those MTPs that associated with the non-target cell-type). Means of carrying out such methods will be known to those skilled in the art. Typically, library members incapable of binding to the target cell population of interest are removed by washing or other methods known to those skilled in the art. Surface bound library members are then removed from the cell surface by a non-specific protease such as trypsin, or a nuclease such as DNaseI, or a combination of both or by any other method known to one skilled in the art. As in the above-described methods of the invention, only library members encoding an MTP remain within the cell population. The internalized MTPs may then be recovered and individually characterised by sequencing the associated nucleic acid, expressing or synthesising the encoded MTP to confirm the desired membrane-translocating properties, and possibly also determining the sub-cellular localization of the MTP.

The invention can also be applied to the isolation of MTPs capable of crossing layers of cells such as Caco-2 cells or human epithelium. In vitro generated nucleic acid libraries encoding a plurality of target peptides are synthesised and selected for binding to, penetration of, or internalization into a target cell population of interest such as, by way of example, Caco-2 cells grown in layers. Library members incapable of binding to the target cell population of interest are removed by washing or other methods known to those skilled in the art. Preferably, surface-bound library members are then removed from the cell surface by a non-specific protease such as trypsin, or a nuclease such as DNaseI, or a combination of both or by any other method known to one skilled in the art. Once again, only library members encoding an MTP remain within the cell population and are protected from the protease or nuclease. The internalized MTPs may then be recovered and individually characterised by sequencing the associated nucleic acid, and optionally expressing or synthesising the encoded MTP to confirm the desired epithelial cell layer translocating properties. Alternatively, the cells can be arranged as monolayers on polycarbonate filters and a selection made as described by Stevenson et al. (1999, *Int. J. Pharm.* 177, pp 103-115). In vitro peptide libraries placed on the apical side of the cells can be recovered on the basolateral side if they translocate through the cells. Using such methods it is possible to select MTPs that are capable of crossing biological membranes, such as the gut wall and skin.

MTPs isolated in this manner have utility as oral delivery agents for non-translocating moieties. By way of example, an MTP of the invention can be conjugated to a protein drug such as insulin and formulated in a suitable pharmaceutical composition such that on entering the intestine, the MTP causes translocation of insulin into the blood circulatory system. As a further example, an MTP of the invention can be conjugated to a small molecule and formulated in a suitable pharmaceutical composition such that on entering the intestine, the MTP causes translocation of the small molecule drug into the blood circulatory system. In yet another example, the MTP may be coated onto the surface of a nanoparticle containing a protein, peptide or small molecule drug in a suitable pharmaceutical composition such that on entering the intestine, the MTP causes translocation of the nanoparticle into the blood circulatory system.

In an alternative composition of the invention, an MTP and its associated non-targeting moiety (i.e. a therapeutic molecule) is mixed with a population of liposomes (i.e. a lipid vesicle or other artificial membrane-encapsulated compartment), to create a therapeutic population of liposomes that contain the MTP and the therapeutic molecule. The therapeutic population of liposomes can then be administered to a patient by e.g. intra-venous injection. Where it is necessary for the therapeutic liposome composition to target specifically a particular cell-type, the liposome composition may additionally be formulated with an antibody domain or the like, which recognises the target cell-type. Such methods are known to the person of skill in the art.

The MTPs according to the invention and MTPs conjugated to non-translocating peptides may be produced by recombinant DNA technology and standard protein expression and purification procedures. Thus, the invention further provides nucleic acid molecules that encode the MTPs, derivatives thereof, or therapeutic molecules according to the invention. For instance, the DNA encoding the relevant peptide can be inserted into a suitable expression vector (e.g. pGEM®, Promega Corp., USA), and transformed into a suitable host cell for protein expression according to conventional techniques (Sambrook J. et al, Molecular Cloning: a Laboratory Manual, Cold Spring Harbor Press, Cold Spring Harbor, N.Y.). Suitable host cells are those that can be grown in culture and are amenable to transformation with exogenous DNA, including bacteria, fungal cells and cells of higher eukaryotic origin, preferably mammalian cells. Alternatively, MTPs may be synthesised in vitro using a suitable in vitro (transcription and) translation system (e.g. the E. coli S30 extract system, Promega corp., USA).

The term "operably linked", when applied to DNA sequences, for example in an expression vector or construct indicates that the sequences are arranged so that they function cooperatively in order to achieve their intended purposes, i.e. a promoter sequence allows for initiation of transcription that proceeds through a linked coding sequence as far as the termination sequence.

Having selected and isolated an MTP, a functional group such as a therapeutic molecule may then be attached to the MTP by any suitable means. As discussed hereinbefore, an MTP may be conjugated to any suitable form of therapeutic molecule, such has an antibody, enzyme or small chemical compound. A preferred form of therapeutic molecule is an siRNA molecule capable of inducing RNAi in a target cell. Typically a chemical linker will be used to link an siRNA molecule to a peptide, such as an MTP. For example, the nucleic acid or PNA can be linked to the peptide through a maleimide-thiol linkage, with the maleimide group being on the peptide and the thiol on the nucleic acid, or a disulphide link with a free cysteine group on the peptide and a thiol group on the nucleic acid.

Pharmaceutical formulations and compositions of the invention are formulated to conform with regulatory standards and can be administered orally, intravenously, topically, or via other standard routes. The pharmaceutical compositions may be in the form of tablets, pills, lotions, gels, liquids, powders, suppositories, suspensions, liposomes, microparticles or other suitable formulations known in the art.

Accordingly, the invention also encompasses the use of an MTP isolated by the methods of the invention in a therapeutic or diagnostic treatment. In particular, the invention provides the use of an MTP to deliver a non-translocating moiety (as described hereinbefore) to one or more populations of membrane-encapsulated compartments. Preferably, the membrane-encapsulated compartment is a liposome or one or more populations of cell types. Particularly preferred is the use of an MTP according to the invention for delivering a non-translocating moiety, especially a therapeutic molecule, such as an siRNA molecule, to a target cell type or population. The target cell or cell population may be in vivo, i.e. in an animal or human subject, or ex vivo, i.e. removed from the animal or human subject to be reintroduced thereto, or in the alternative, the cell, cell population or liposome is in vitro. Any route of administration known to the person of skill in the art could be used. Particularly, a route of administration that is preferred for the target cell type or population should preferably be used. For example, preferred routes of administration to the subject or patient include subcutaneous injection, ingestion or suppository.

By way of example, to treat a viral infection in a subject, an MTP of the invention may be conjugated to a suitable antiviral agent, and the MTP and antiviral molecule can then be administered to the subject either naked or comprised in an artificial liposome, for example. Similarly, where a subject is suffering from a cellular disease such as cancer, an MTP of the invention may be conjugated to an appropriate anti-cancer molecule/drug, such as an siRNA molecule or other therapeutic entity, and administered via an appropriate administration route to the subject. The MTPs can also be used to deliver themselves or a non-translocating moiety to a bacterial cell. Thus, a bacterial infection can be treated in a subject, by conjugating an MTP of the invention to an anti-bacterial agent.

Further in this regard, it is sometimes necessary for a therapeutic composition, such as an MTP conjugated to a therapeutic molecule to be delivered to a specific cell type or population in a subject. This can be achieved ex vivo, for example, by adding the therapeutic composition to a population of cells that have been previously removed from the subject or patient. Alternatively, the MTP can be selected, as previously described, to translocate into a specific cell type or cell types, as required. In a further alternative, the MTP may be directly conjugated to an antibody molecule, an antibody fragment (e.g. Fab, F(ab)$_2$, scFv etc.) or other suitable targeting agent, so that the MTP and any additional conjugated moieties are targeted to the specific cell population required for the treatment or diagnosis. In yet another alternative embodiment, the MTP and its associated non-translocating moiety may be comprised in a liposome population, wherein the liposomes (e.g. the liposome membranes) additionally comprise an appropriate targeting moiety, such as an antibody or antibody fragment. The resultant liposomes may then be suitably administered to the subject or patient.

Preferably in the uses described above, the MTP is conjugated to the non-translocating moiety or therapeutic molecule via an interaction that is cleavable inside the target cell type, e.g. by way of an enzymatic cleavage or due to the reducing intracellular environment.

The invention will now be further illustrated by way of the following non-limiting examples.

EXAMPLES

Unless otherwise indicated, commercially available reagents and standard techniques in molecular biological and biochemistry were used.

Materials and Methods

The following procedures used by the present applicant are described in Sambrook, J. et al., 1989 supra.: analysis of restriction enzyme digestion products on agarose gels and preparation of phosphate buffered saline.

General purpose reagents were purchased from SIGMA-Aldrich Ltd (Poole, Dorset, U.K.). Oligonucleotides were obtained from Eurogentec Ltd (Southampton, U.K.). Amino acids, and S30 extracts were obtained from Promega Ltd (Southampton, Hampshire, U.K.). Vent and Taq DNA polymerases were obtained from New England Biolabs (Cambridgeshire, U.K.). FITC labelled peptides were obtained from Pepscan Systems (Lelystad, Netherlands).

Example 1

(i) Construction of a Cis Display Library for Selection of MTPs

Library construction and in vitro transcription and translation were carried out as described by Odegrip et al. (2004, Proc. Natl. Acad. Sci. USA, 101 2806-2810).

The tac-NNB-RepA-CIS-ori PCR construct was prepared by appending an 18-mer NNB library (where N is any nucleotide and B is either C, T or G) to the tac promoter by PCR and then ligating it to the RepA-CIS-ori region followed by PCR amplification.

(ii) Selection of Cell Membrane-Translocation Competent Peptides

In vitro transcription and translation was performed with 2 µg of library DNA in an E. coli S-30 lysate system for up to 30 minutes at 30° C. and then diluted with blocking buffer (1% BSA in PBS). Typically, 2 µg of linear DNA was added per 50 µl of S-30 lysate. The expressed library was added to 5 µl of PBS washed human red blood cells (RBC) and incubated on ice for 30 minutes. RBC were centrifuged at 2000 rpm for 5 min and supernatant removed.

The RBC pellet was resuspended in 200 µl of PBS supplemented with 2 mM $CaCl_2$, 2 mM MgCl and 1 µg of DNase 1 and incubated at room temperature for 15 minutes. The cells were washed once with PBS by centrifugation to form a loose pellet and then resuspended in 200 µl PBS. The RBC suspension was layered over 200 µl of dibutyl pthalate and centrifuged at 11000 rpm for 4 minutes. The aqueous phase was removed and the RBC pellet gently pipetted from the oil and resuspended in 100 µl of PBS.

Cells were lysed in 500 µl of PB buffer (Qiagen), and the DNA was purified using Qiagen columns and then resuspended in 50 µl of sterile water.

In a parallel selection, the RBC pellet was treated with 1 µg/ml of trypsin at 37° C. for 30 min instead of DNaseI, at which point the cells were spun, the supernatant removed and the pellet resuspended in 200 µl of PBS. The cells were then spun through dibutyl phthalate and DNA recovered as described above for DNase treated cells.

The N-terminal library region was amplified separately from both selections and reassembled with the RepA-CIS-ori, as described by Odegrip et al. (2004, Proc. Natl. Acad. Sci. USA, 101 2806-2810), to produce input DNA for the next round of selection. After five rounds of selection, recovered DNA was amplified using PCR, purified and digested with NotI and NcoI. The DNA was then ligated into a similarly digested M13 gpVIII phagemid vector and transformed into E. coli XL-1 blue cells, and plated on 2% glucose, 2×TY, 100 µg/ml ampicillin plates. Individual colonies were grown overnight and phagemid DNA was isolated and sequenced to determine the peptide sequence.

(iii) Analysis of Membrane-Translocation Competence

Selected peptides were synthesized labelled with FITC at the N-terminus and analysed by FACS for cell association using Jurkat cells. Jurkat cells (100000) were washed twice in PBS, incubated with 1 µg of labelled peptide in 100 µl PBS supplemented with 1% foetal calf serum for 15 minutes at room temperature, and washed twice in PBS and analysed in a Becton Dickinson FACS analyzer. Peptides associated with cells were then viewed by fluorescence microscopy without fixation to monitor internalization into cells.

Nine out of twenty-three peptides were cell associated. Examples of these are shown in FIG. 1.

FIG. 1 shows fluorescent microscopy and FACS analysis of non-fixed Jurkat cells. Peptides 7, 13, and 19 are examples of membrane-translocating peptides isolated by the method described. Labelling can be seen by the fluorescence within the cells as observed by microscopy (left and central photos) and the fluorescence intensity of the cells by FACS (plot chart on the right). The FACS analysis plot chart shows FITC-fluorescence (x-axis) against counts of cells (y-axis). Peptide 24 is a negative control FLAG epitope peptide, which does not cause cells to fluoresce as analysed by microscopy or by FACS.

As described above, parallel selections were performed with either DNaseI or trypsin to remove membrane bound or non-translocated peptide-repA-DNA complexes from contaminating the recovery of MTPs after lysis of the cells. The internalised peptide-repA-DNA complexes would be resistant to treatment with either of these enzymes. In the alternative methods, either DNaseI was used to digest the repA DNA so that this could not be amplified, or trypsin was used to digest the peptide-repA protein and any potential protein-protein interactions. Both methods were found to be successful in allowing the selection of the desired MTPs.

(iv) Sequence Analysis of MTP's

A membrane translocation competent peptide (MTP) was selected for sequence analysis to determine whether the translocation competent peptide sequence had any sequence similarities to known membrane-translocating motifs. The result is shown in FIG. 2.

As shown, the selected peptide (denoted D4, top row, SEQ ID NO: 1) showed some sequence homology (as indicated in the middle row) to the known membrane-translocating motif of the HIV-TAT protein (bottom row).

The results further demonstrate the efficacy of the selection method described for isolating compounds that exhibit cell-membrane translocation activity.

It is interesting to note, however, that other MTPs isolated according to the methods described did not show sequence homology to known translocating domains. This allows the identification of new classes of MTPs.

Example 2

(i) Construction of a Cis Display Library for Selection of MTPs

The following example describes the selection of MTPs that are capable of crossing or penetrating synthetic lipid membranes. Library construction and in vitro transcription and translation are carried out as described in Example 1 above.

(ii) Selection of Synthetic Membrane-Translocation Competent Peptides

In vitro transcription and translation are performed as described in Example 1 above.

Emulsions of artificial oil compartments are made by slowly adding 50 µl PBS (in 10 µl aliquots) to 0.5 ml ice cold 0.5% Triton X-100 and 4.5% Span 80 (sorbitane trioleate) in light mineral oil on ice stirred at 1600 r.p.m. for 5 minutes. The emulsion mix is then spun at 3000 g for 5 minutes and the oil phase removed to leave the emulsion at the bottom of the tube. The in vitro transcription and translation mix is then added to the emulsion mix in 1 ml PBS and mixed by gently inverting five times and incubating on ice for 30 minutes.

2.5 µg of DNaseI is then added with 2 mM $CaCl_2$ and 2 mM MgCl (final concentration) and incubated at room temperature for 15 minutes. Alternatively, to adding DNaseI, 1 µg/ml of trypsin can be added and incubated at 37° C. for 30 minutes.

The emulsion is washed 5 times by adding 1 ml PBS and centrifuging at 3000 g for 5 minutes, removing the wash solution each time. The emulsion is broken and washed by adding 1 ml hexane, vortexing, briefly centrifuging, and then removing the hexane layer. This washing step can be repeated one or two more times and the residual hexane is removed by drying in a Speedvac (Farmingdale, N.Y.) for 5 minutes at room temperature.

The DNA can be recovered by addition of 100 µl PB buffer (Qiagen) and the DNA can be prepared for the next round of selection as described in Example 1.

The selection process is repeated, for example, 5 times before cloning the DNA into phage as described in the Example 1 above.

Peptide sequences can be identified by sequencing and the peptides tested as described in Example 1.

---

---

The invention claimed is:

1. A method for isolating a membrane-translocating peptide (MTP) from an in vitro peptide library, comprising the steps of:
   a) forming the in vitro peptide library comprising a plurality of nucleic acid-peptide complexes, each peptide of the nucleic acid-peptide complex comprising a candidate membrane translocation peptide by:
   expressing in vitro a plurality of nucleic acid constructs, each nucleic acid construct comprising a nucleic acid target sequence and a promoter sequence operably linked to a nucleic acid coding sequence, said nucleic acid coding sequence encoding a peptide of between 2 and 50 amino acid residues and a nucleic acid binding peptide capable of binding in cis to the nucleic acid target sequence, such that expression of the nucleic acid coding sequences leads to formation of the plurality of nucleic acid-peptide complexes through cis-binding of the nucleic acid binding peptide to the nucleic acid target sequence,
   b) incubating the in vitro peptide library with a population of membrane-encapsulated compartments under conditions designed to allow translocation into the compartment by the nucleic acid-peptide complexes;
   c) removing any nucleic acid-peptide complexes that remain unassociated with the membrane-encapsulated compartments;
   d) removing nucleic acid-peptide complexes that are bound to the surface of the membrane-encapsulated compartments, but which have not been internalized by exposing the membrane-encapsulated compartments to a protease or a nuclease;
   e) recovering any internalized nucleic acid-peptide complexes from within the membrane-encapsulated compartments; and
   f) isolating and characterising the peptide encoded by the nucleic acid of the internalized nucleic acid-peptide complex.

2. The method according to claim 1, wherein the population of membrane-encapsulated compartments is a population of naturally occurring cells.

3. The method according to claim 1, wherein the population of membrane-encapsulated compartments is a population of liposomes.

4. The method according to claim 1, wherein non-membrane associated peptide-nucleic acid complexes are separated from the membrane-encapsulated compartments by centrifugation of the compartments through a non-aqueous layer.

5. The method according to claim 4, wherein the non-aqueous layer is mineral oil.

6. The method according to claim 1, wherein the nucleic acid binding peptide is RepA and the nucleic acid target sequence is an origin of replication that is recognized by the RepA protein (ori).

7. The method according to claim 1, further comprising the step of correlating the peptide of the nucleic acid-peptide complex of step e with the sequence of the nucleic acid construct of the nucleic acid-peptide complex, thereby identifying the nucleic acid sequence encoding a membrane-translocating peptide.

8. The method according to claim 1, wherein the peptide comprises an amino acid sequence selected from the group consisting of between 2 and 25 residues in length; and between 2 and 20 residues in length.

9. The method of claim 7, further comprising isolating the nucleic acid construct and inserting it into an expression vector or construct.

10. The method of claim 1, wherein:
the plurality of nucleic acid constructs are expressed from an *E. coli* S-30 lysate system;
the promoter sequence is the tac promoter; and
the population of membrane encapsulated compartments comprise human red blood cells (RBCs).

11. The method of claim 1, wherein:
the plurality of nucleic acid constructs are expressed from an *E. coli* S-30 lysate system;
the tac promoter sequence is the tac promoter; and
the population of membrane-encapsulated compartments is formed by adding an aqueous buffer to a mixture of polyethylene glycol p-(1,1,3,3-tetramethylbutyl)-phenyl ether (TRITON X-100™) and sorbitane monooleate (SPAN™ 80).

12. The method of claim 1 wherein a membrane of the membrane-encapsulated compartments comprises aliphatic molecules.

* * * * *